(12) United States Patent
Douglas

(10) Patent No.: US 11,003,948 B1
(45) Date of Patent: May 11, 2021

(54) OPTIMIZED IMAGING CONSULTING PROCESS FOR RARE IMAGING FINDINGS

(71) Applicant: Robert Edwin Douglas, Winter Park, FL (US)

(72) Inventor: Robert Edwin Douglas, Winter Park, FL (US)

(*) Notice: Subject to any disclaimer, the term of this patent is extended or adjusted under 35 U.S.C. 154(b) by 0 days.

(21) Appl. No.: 17/072,350

(22) Filed: Oct. 16, 2020

Related U.S. Application Data

(63) Continuation-in-part of application No. 16/842,631, filed on Apr. 7, 2020.

(60) Provisional application No. 62/916,262, filed on Oct. 17, 2019.

(51) Int. Cl.
*G06K 9/62* (2006.01)
*G06T 7/00* (2017.01)
*G06K 9/00* (2006.01)
*G16H 30/40* (2018.01)
*G16H 30/20* (2018.01)

(52) U.S. Cl.
CPC ....... *G06K 9/6227* (2013.01); *G06K 9/00315* (2013.01); *G06K 9/00597* (2013.01); *G06K 9/626* (2013.01); *G06K 9/6263* (2013.01); *G06T 7/0012* (2013.01); *G16H 30/20* (2018.01); *G16H 30/40* (2018.01)

(58) Field of Classification Search
CPC .............. G06K 2209/05; G06K 9/6254; G06K 9/6262; G06K 9/6267; G16H 30/20
See application file for complete search history.

(56) References Cited

U.S. PATENT DOCUMENTS

| | | | | |
|---|---|---|---|---|
| 2006/0282336 A1* | 12/2006 | Huang | ............... | G06Q 30/0633 705/26.61 |
| 2012/0166546 A1* | 6/2012 | Venon | .................... | G16H 40/67 709/205 |
| 2019/0171915 A1* | 6/2019 | Reicher | ............... | G06F 3/04842 |

* cited by examiner

*Primary Examiner* — Ross Varndell

(57) ABSTRACT

In this patent, a smart consulting process is established to improve workflow and human classification of images. A key innovative aspect is the process for selecting an optimal consultant for an image. Such a process may improve human image classification, such as diagnostic radiology. Furthermore, such a process may improve education to more novice imagers. A modified workflow is established where users have general and specific consult pools. Additionally, a modified relative value unit (RVU) system is created to appropriately compensate users for the modified workflow, which is established.

20 Claims, 13 Drawing Sheets

PRIOR ART

SMART IMAGE CONSULTING PROCESS

LIST OF FACTORS INDICATING THAT A FIRST USER NEEDS HELP WITH IMAGE CLASSIFICATION

List of factors of a first user needing help

- Help button
- Facial recognition
- Eye tracking
- Difference in opinion from radiologist and AI per RAML
- Consulting request (e.g., arrow(s), 3D cursor(s))

Fig. 4

MULTI-MARK UP, MULTI-CONSULTANT PROCESS AND AN EXAMPLE

Fig. 7A

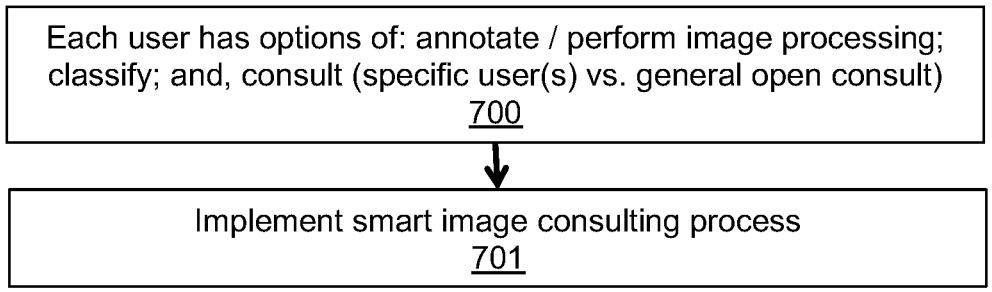

Each user has options of: annotate / perform image processing; classify; and, consult (specific user(s) vs. general open consult)
700

↓

Implement smart image consulting process
701

Fig. 7B

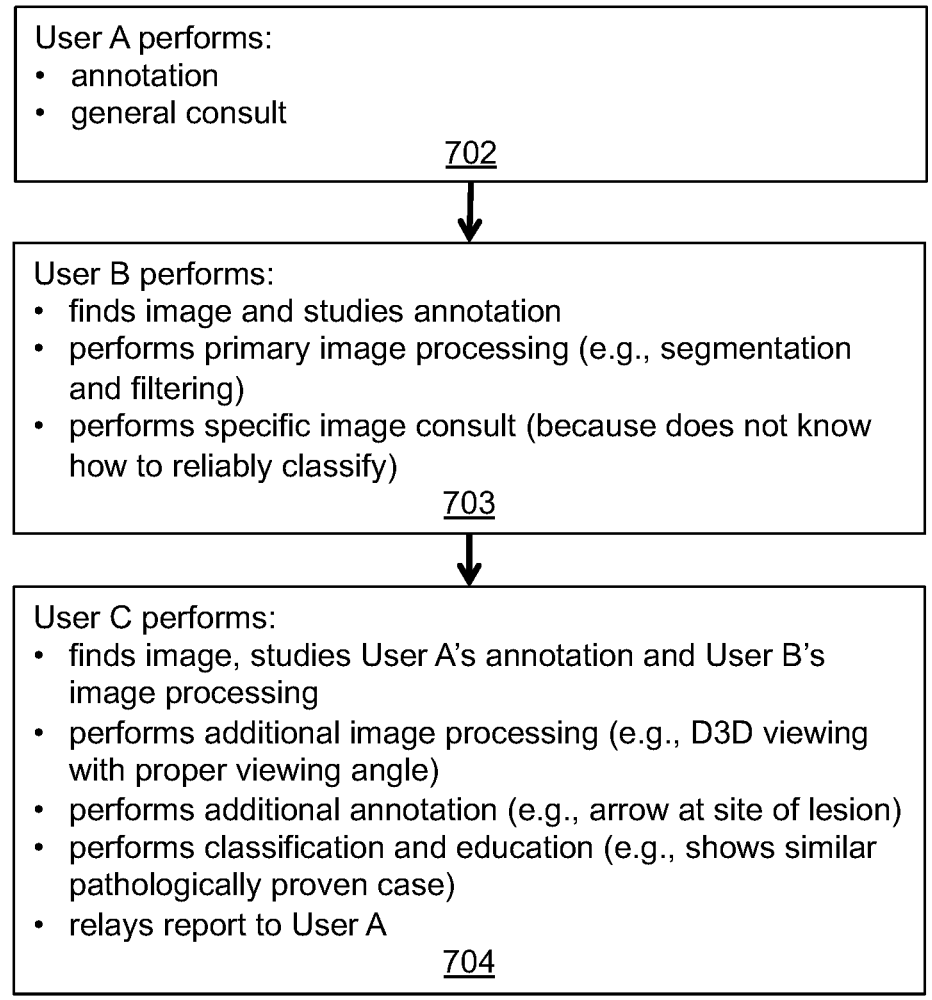

User A performs:
- annotation
- general consult

702

User B performs:
- finds image and studies annotation
- performs primary image processing (e.g., segmentation and filtering)
- performs specific image consult (because does not know how to reliably classify)

703

User C performs:
- finds image, studies User A's annotation and User B's image processing
- performs additional image processing (e.g., D3D viewing with proper viewing angle)
- performs additional annotation (e.g., arrow at site of lesion)
- performs classification and education (e.g., shows similar pathologically proven case)
- relays report to User A

704

MULTI-USER IMAGE ANALYSIS AND REPORTING

EXAMPLES OF IMAGE VIEWING STRATEGIES DURING THE MULTI-MARK UP, MULTI-CONSULTANT PROCESS

Viewing strategies

- Conventional viewing strategies (e.g., modifying the visual representation, such as changing the color and tranparency, filtering, etc.)
- Advanced viewing strategies (e.g., US Patent 10,586,400, PROCESSING 3D MEDICAL IMAGES TO ENHANCE VISUALIZATION)
- Interaction of 3D dataset with geo-registered tools, as described in US Patent 10,712,837, USING GEO-REGISTERED TOOLS TO MANIPULATE THREE-DIMENSIONAL MEDICAL IMAGES
- Interaction of 3D dataset with virtual tools, as described in PCT/US19/47891, A VIRTUAL TOOL KIT FOR 3D IMAGING
- "Ghost imaging" per US Patent Application 16/010,925, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING
- Flow visualization features, as described in US Patent Applications 16/506,073, A METHOD FOR ILLUSTRATING DIRECTION OF BLOOD FLOW VIA POINTERS, and 16/779,658, 3D IMAGING OF VIRTUAL FLUIDS AND VIRTUAL SOUNDS
- Voxel manipulation strategies, per US Patent Application 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION

Fig. 9

ALGORITHM THAT FINDS THE MOST APPROPRIATE CONSULT
- Not disturb others from work
- Analyze past reports of each user in the group
- Analyze past images of each user in the group
- Analyze past consult patterns
- Analyze feedback from past consult patterns (e.g., satisfaction scores)
- Urgency of the case
- Option to exclude user(s)
- See which user(s) are available

```
Radiologist #456
General radiologist with special skill of
asbestos related lung disease
*Needs help with temporal bone
1100
```

Fig. 11B

```
Radiologist #911
Neuroradiologist with
specialty skills of cerebral
vasculitis
1101
```

```
Radiologist #415
Neuroradiologist with
specialty skills of
phakomatoses
1104
```

```
Radiologist #316
Neuroradiologist with
specialty skills of PET
imaging of dementia
1102
```

```
Radiologist #899
Neuroradiologist with
specialty skills of temporal
bone lesions
1105
```

```
Radiologist #200
Neuroradiologist with
specialty skills of skull base
tumors
1103
```

Fig. 11C

```
Radiologist #322
Musculoskeletal radiologist with special
skill of metabolic bone disease
*Connects Radiologist 456 with 899
1106
```

RVU MODIFIED BASED ON IMAGE DIFFICULTY

- Imaging finding
    - Presence of athology
- Patient history (e.g., indication of study)
- Patient labs (e.g., WBC of 20)
- Urgency of exaimation
- Consulting process

Fig. 12

| Unread Examinations | General (open to anyone) cases needing consultation | Specific (only seen by you) cases needing consultation |
|---|---|---|
| - | - | - |
| - | - | - |
| - | - | - |
| - | - | - |
| - | - | - |
| - | - | - |
| - | - | - |
| - | - | - |

Fig. 13

OPTIMIZED IMAGING CONSULTING PROCESS FOR RARE IMAGING FINDINGS

CROSS REFERENCE TO RELATED APPLICATIONS

This application is a continuation in part of U.S. patent application Ser. No. 16/842,631 filed on Apr. 7, 2020 and also claims the benefit of U.S. Provisional 62/916,262 filed on Oct. 17, 2019.

TECHNICAL FIELD

Aspects of this disclosure are generally related to use of distribution of work.

INTRODUCTION

There are multiple subspecialties within the field of radiology. For example, the subspecialties include: neuro-radiology; nuclear medicine; musculoskeletal radiology; cardiac radiology; and mammography. An imaging examination such as a CT scan of the chest, abdomen and pelvis can contain multiple abnormalities. For example, there could be an abnormality of the spine, which would best be evaluated by a neuroradiologist and an abnormality of the liver, which would best be evaluated by an abdominal imaging radiologist.

SUMMARY

All examples, aspects and features mentioned in this document can be combined in any technically conceivable way.

First, we will explain the problem that this patent overcomes. You have an image. You have a finding. You don't know what the finding is? How to classify it? You don't know who can solve it. How to find the right person? In this patent, a solution to the above problem is provided. In a broad sense, a general and specific user pool is created, along with a point system for the reward.

Further, this patent improves on PCT/US2019/023968, RADIOLOGIST ASSISTED MACHINE LEARNING, filed on Mar. 26, 2019 because this patent provides an optimal consultation strategy. In Patent Application PCT/US2019/023968, RADIOLOGIST ASSISTED MACHINE LEARNING, filed on 26 Mar. 2019, a process wherein radiologists would work in a more collaborative environment was described. More specifically, a CT scan of the abdomen could be divided up into multiple different sub-volumes. Then, each sub-volume analyzed and passed to different virtual buckets. Some situations where there was a difference in opinion from the artificial intelligence system and the radiologist were also described. In these situations, a process of passing the volume to another radiologist for a second opinion could be performed. Options included are manual consultation process and using computer algorithms (e.g., AI) to perform the consultations. For example, an artificial intelligence system can perform predictions on who to send the images to based on age, gender, type of scan, and feedback from past consultation patterns. Thus, this patent improves on the current process for image analysis by developing a smart peer-to-peer consulting process. This patent application improves on the prior art by improving the workflow and is therefore useful.

In accordance with an aspect, the preferred method comprises a method comprising: reviewing, by a first user, an image; selecting a second user from a group of users wherein the second user is qualified to classify the image; upon an input from the first user, presenting the image to the second user; reviewing, by the second user, the image; and presenting the second user's classification of the image to the first user.

Some embodiments comprise sending the image into a bin where the group of users can view the image.

Some embodiments comprise wherein the second user performs selection of the second user. Some embodiments comprise wherein a third user performs selection of the second user.

Some embodiments comprise wherein a set of characteristics is used to select the second user. The set of characteristics may include prior image classifications, prior images and feedback from past consult patterns wherein feedback comprises the first reviewer rating the quality of the second user's classification. In addition, the set of characteristics includes an availability of each user in the group. In addition, the set of characteristics includes an urgency of the image.

Some embodiments comprise wherein the second user is selected by an artificial intelligence algorithm.

Some embodiments comprise wherein, before presenting the image to the second user, the first user performs at least one of the group comprising: image processing; annotations on the image; and, selecting a portion of the image for analysis. Some embodiments comprise wherein, before presenting the classification to the first user, the second user performs at least one of the group comprising: image processing; annotations on the image; selecting a portion of the image for analysis; and, presentation of the image to at least one additional user.

Some embodiments comprise wherein the second user performs a teaching session to the first user wherein the teaching session comprises at least one of the group of: image processing; and, image annotation.

Some embodiments comprise wherein the selecting a second user occurs based on an input from the first user wherein the input consists of at least one of the group of: activating, by the first user, a help button; activating, by the first user, a consult request; detecting, by a camera, that the first user has a predetermined facial expression; detecting, by a camera, that the first user has a predetermined eye pattern; detecting, by a camera, that the first user has a predetermined combination of facial expression and eye pattern; and detecting, by a computer algorithm, that there is a difference between the first user's classification and a classification by an artificial intelligence algorithm.

Some embodiments comprise a reward system to at least one of the group comprising: the first user; the second user; and, an additional user.

Some embodiments comprise generating a modified relative value unit (RVU) of an imaging examination based on the presence of at least one imaging finding in the imaging examination.

Some embodiments comprise a modified relative value unit (RVU) of an imaging examination based on at least one of the group consisting of: indication of the study; laboratory data; consultations; and, urgency of the study.

Some embodiments comprise the classification accuracy of users in the group is determined.

Some embodiments comprise wherein a report indicates image consult.

BRIEF DESCRIPTION OF THE FIGURES

FIG. 4 illustrates an example table illustrating a list of factors indicative of a first user needing help.

FIG. 7A illustrates a multi-mark up, multi-consultant process.

FIG. 7B illustrates an example of the multi-mark up, multi-consultant process.

FIG. 9 illustrates examples of image viewing strategies during the multi-mark up, multi-consultant process.

FIG. 10 illustrates criteria that an algorithm can use to find the most appropriate consult.

FIG. 11A illustrates features of a first user who needs help with a neuroradiology imaging examination.

FIG. 11B illustrates features of a five users who have expertise in neuroradiology.

FIG. 11C illustrates the connection of the first user with the optimum consultant.

FIG. 12 illustrates a modified relative value unit (RVU) system based on factors other than just type of imaging examination.

FIG. 13 illustrates a worklist for radiologists.

DETAILED DESCRIPTIONS

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

Figure 1:
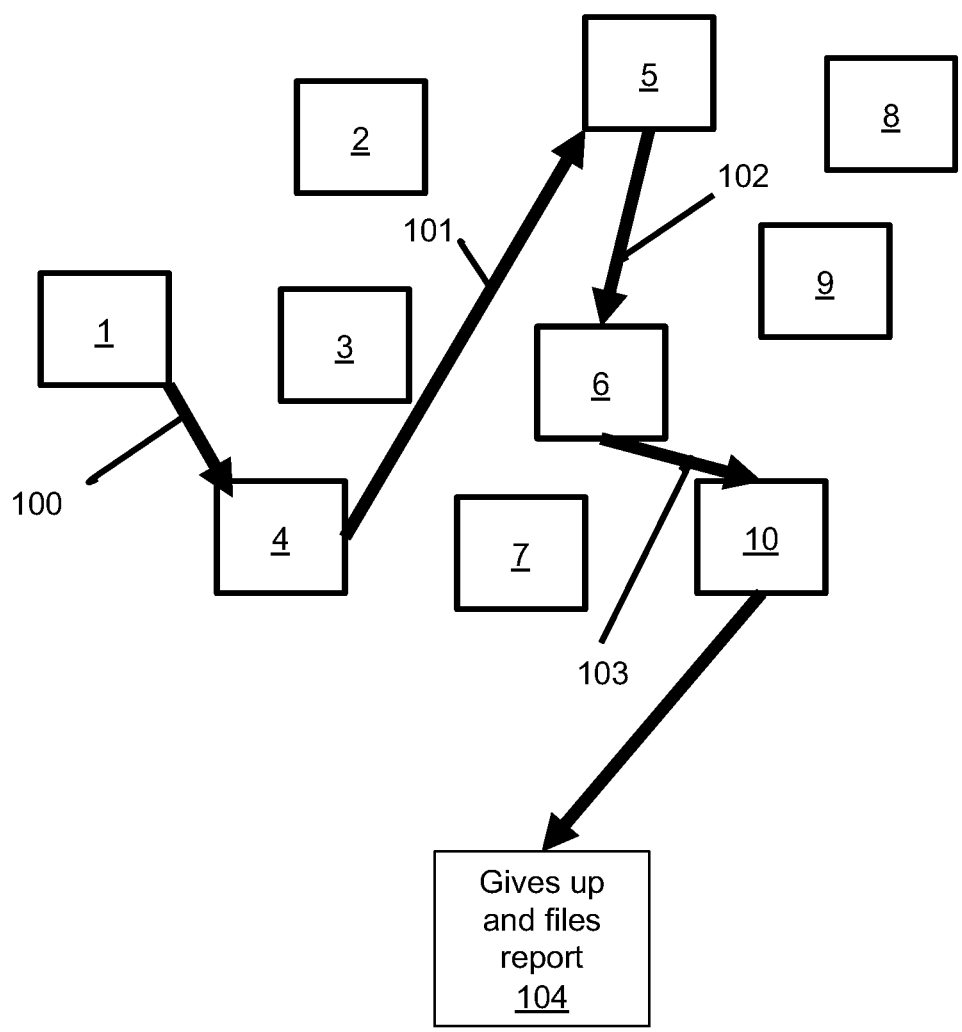
FIG. 1 illustrates the current image consulting process.

FIG. 1 illustrates the current image consulting process. 1 illustrates a radiologist, who is currently examining an image and has a question (e.g., he/she does not know how to interpret an imaging finding). 2, 3, 4, 5, 6, 7, 8 and 10 illustrates radiologists who also do know not know how to interpret the imaging examination. 9 illustrates a radiologist who confidently knows exactly how to answer the question that radiologist 1 has. Note that radiologist 1 communicated 100 (e.g., by phone, text message pop up, or walking over to the station) to radiologist 4. After reviewing the images, radiologist 4 did not know the answer. Radiologist 1 then communicated 101 over to radiologist 5. After reviewing the images, radiologist 5 did not know the answer. Radiologist 1 then communicated 102 over to radiologist 6. After reviewing the images, radiologist 6 did not know the answer. Radiologist 1 then communicated 103 over to radiologist 10. After reviewing the images, radiologist 10 did not know the answer. At this juncture, radiologist 1 has made 4 attempts. All of which are unsuccessful since radiologists 4, 5, 6 and 10 did not know the answer. Radiologist then proceeded to give up and file the file the report 104. Note that in this scenario, radiologists 2, 3, 7, 8 and 9 were never asked. Note that radiologist 9 knew the answer, but was never asked. This illustration is important because the optimum consultant (radiologist 9) was not identified.

Figure 2:
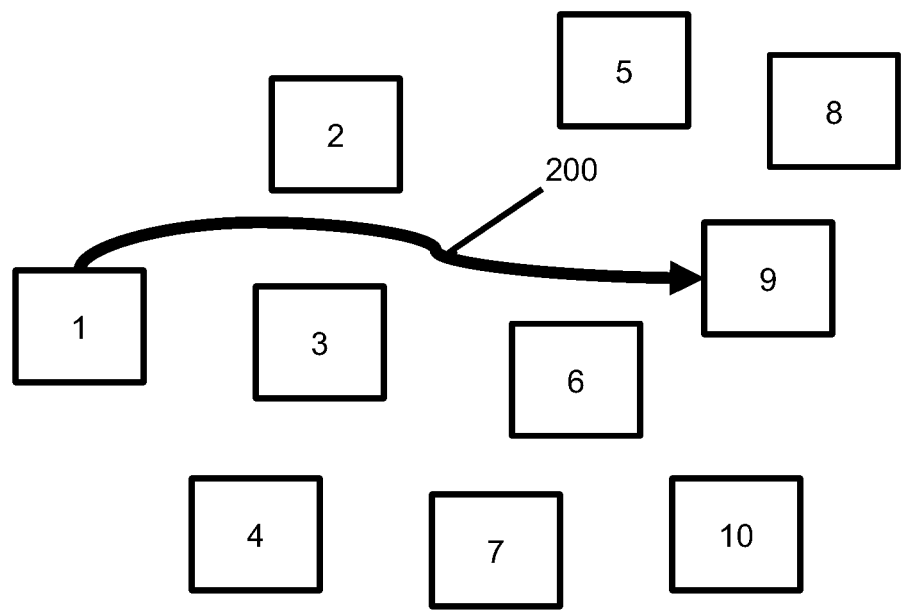
FIG. 2 illustrates the current image consulting process.

FIG. 2 illustrates the current image consulting process. 1 illustrates a radiologist, who is currently examining an image and has a question (e.g., he/she does not know how to interpret an imaging finding). Radiologist 1 implements the smart consult process described in this patent and the image is passed 200 to radiologist 9 who knowns the imaging finding confidently. 2, 3, 4, 5, 6, 7, 8 and 10 illustrates radiologists who also do not know how to interpret the imaging examination and were not consulted.

Figure 3:
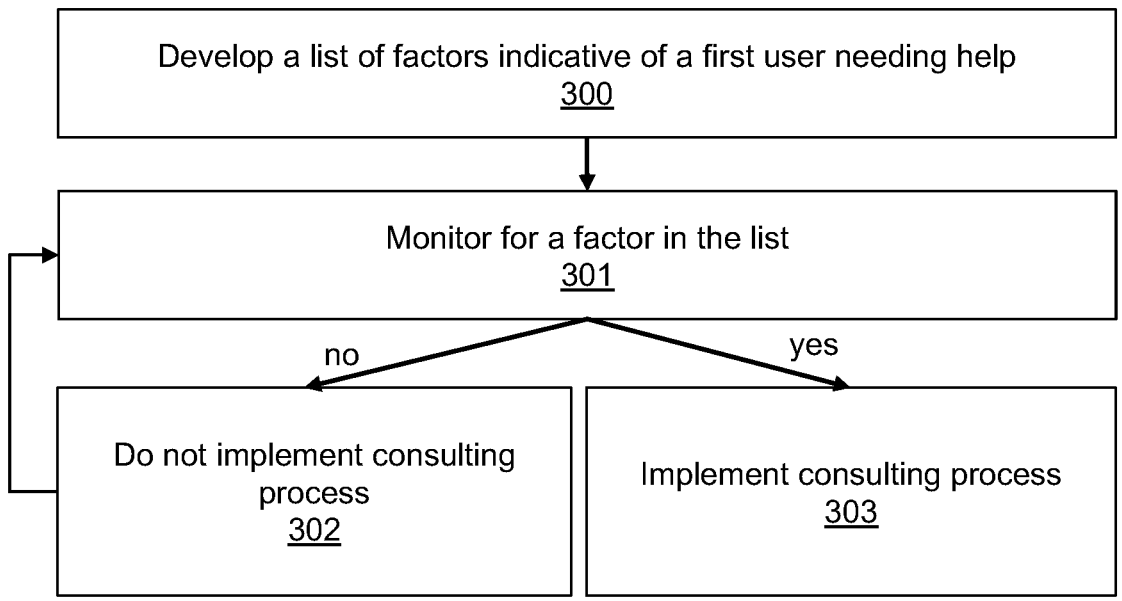
FIG. 3 illustrates when to implement the consulting process.

FIG. 3 illustrates when to implement the consulting process. 300 illustrates a processing block of developing a list of factors indicative of a first user needing help with an image. 301 illustrates a processing block of monitoring for a factor in the list. 302 illustrates a processing block which occurs when no factor is identified and wherein the consulting process is not implemented and wherein processing block 301 of monitoring for a factor in the list continues. 303 illustrates a processing block of implementing the consulting process, which is described subsequently in this patent.

FIG. 4 illustrates an example table illustrating a list of factors indicative of a first user needing help. There are several options. First, the first user could have a "help" button on their display or a help setting on their computer, which could be turned on or off. This is useful because if the first user does not want to receive help (e.g., dictating routine chest x-rays and is comfortable with all of the imaging findings and interpretation thereof), the help button turned off would (1) prevent unnecessary work from the second user and the third user and (2) prevent any pop ups offering help from the third user, which could distract the first user. Second, a camera can be utilized for real time facial expression recognition of the user who is performing the image analysis. For example, if the facial expression recognition determines that the user is confused, this can be an indicator that the first user needs help. Third, a camera can be utilized for eye tracking of the user who is performing the analysis. If the eye pattern looks too long at a particular imaging finding, then a trigger can be set for the first user needing help, as described in U.S. patent application Ser. No. 16/842,631, A SMART SCROLLING SYSTEM, which is incorporated by reference in its entirety. In some embodiments, eye tracking metrics and facial expressions can be used together to determine whether a user needs help. Fourth, the difference in opinion from a radiologist and AI algorithm can be utilized to determine whether a user needs help. This process is disclosed in PCT/US2019/023968, RADIOLOGIST ASSISTED MACHINE LEARNING, which is incorporated by reference in its entirety. Fifth, a consulting request can be performed via computer commands, such as placing an arrow or placing a 3D cursor, such as is U.S. Pat. No. 10,795,457, INTERACTIVE 3D CURSOR, which is incorporated by reference in its entirety.

Figure 5:
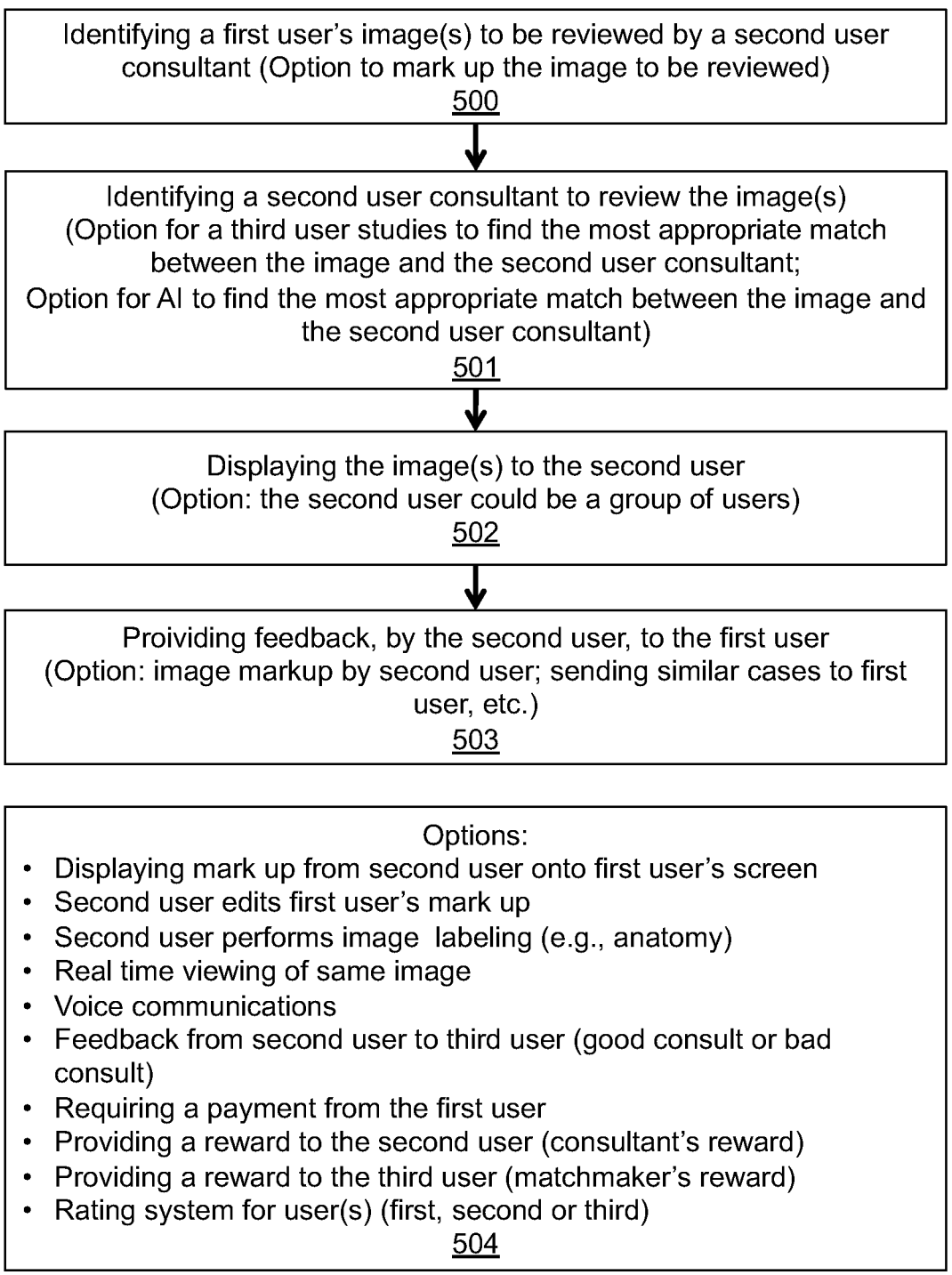
FIG. 5 illustrates implementing the smart image consulting process.

FIG. 5 illustrates implementing the smart image consulting process. 500 illustrates a processing block of identifying image(s) to be reviewed by a second user consultant. Note that there is an option to mark up the image to be reviewed. 501 illustrates a processing block of identifying a second user consultant to review the image(s). Note that there is an option for a third user studies to find the most appropriate match between the image and the second user consultant.

Note that there is also an option for an artificial intelligence (AI) algorithm to find the most appropriate match between the image and the second user consultant. 502 illustrates a processing block of displaying the image(s) to the second user. Note that there is an option for the second user could be a group of users. 503 illustrates a processing block of providing feedback, by the second user, to the first user. Note that there is an option for image markup by second user. Additional feedback from a sending similar cases to first user for training purposes. There are some options. For example, a markup from second user can be displayed onto the first user's screen. A second user edits first user's mark up. A second user performs image labeling (e.g., anatomy). There can be real time viewing of same image (first user watches as second user views image by scrolling, windowing and leveling, etc.). A Voice communication can be implemented to connect the first user and the second user. Feedback from second user to third user (good consult or bad consult) can be performed. A payment (e.g., fraction of RVU from the study paid) from the first user can be utilized. A reward (e.g., fraction of RVU from the study earned) to the second user (consultant's reward) can be provided. A reward to the third user (matchmaker's reward) can be provided. A rating system for user(s) (first, second or third) can be utilized. Some radiologists could therefore earn a portion of their RVUs and even their entire RVUs through consulting work. Some radiologists could therefore earn a portion of their RVUs and even their entire RVUs through "third user" work. For example, a third user could be very good at knowing who to send images to. Feedback from second user to third user (good consult or bad consult) can be used for assessment of third user performance.

Figure 6:
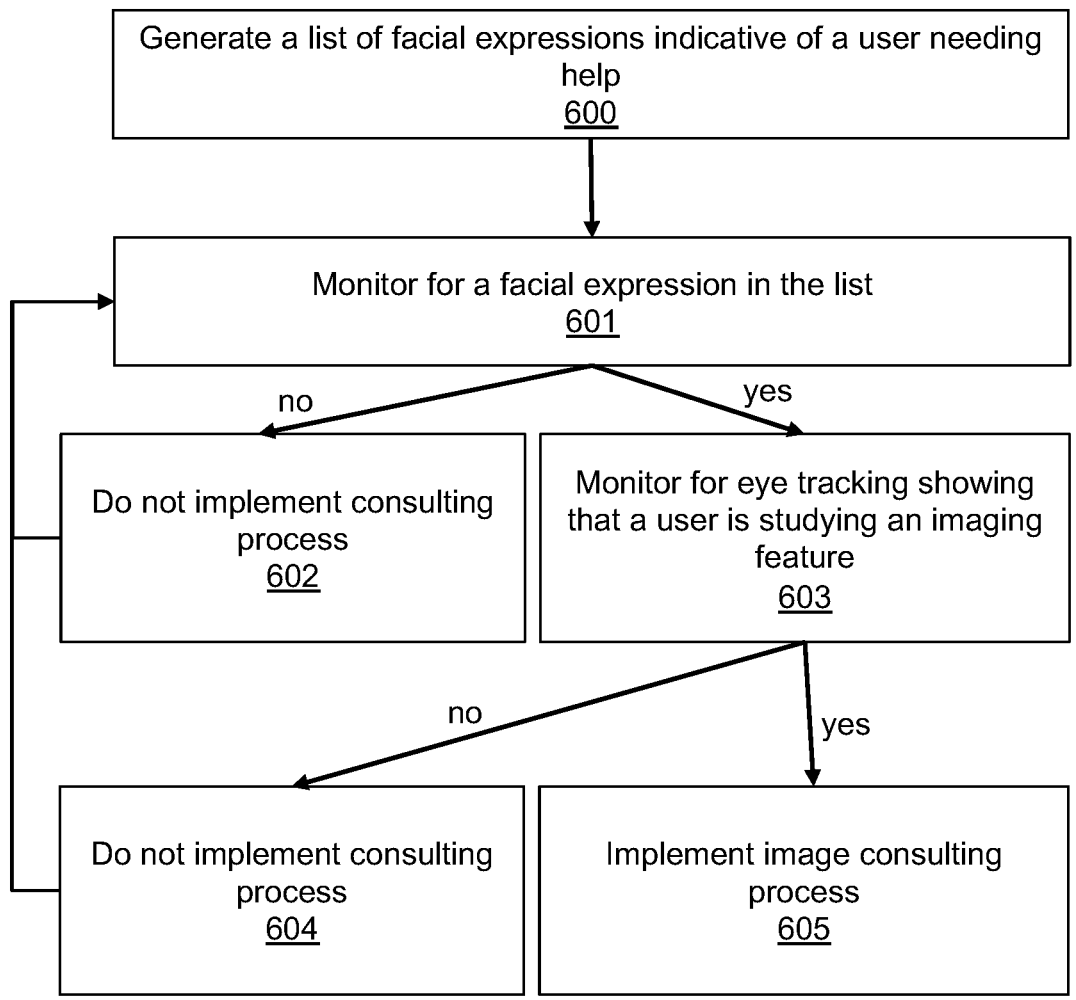
FIG. 6 illustrates when to implement the consulting process.

FIG. 6 illustrates when to implement the consulting process. 600 illustrates a processing block of generating a list of facial expressions indicative of a first user needing help with an image. 601 illustrates a processing block of monitoring for a facial expressions in the list. 602 illustrates a processing block which occurs when no facial expression is identified and wherein the consulting process is not implemented and wherein processing block 601 of monitoring for a facial expression in the list continues. 603 illustrates a processing block of monitoring for eye tracking findings showing that a user is studying an imaging feature which occurs if there is a facial expression on the list. 604 illustrates a processing block which occurs when there is no indication that the user is studying an imaging feature and wherein the consulting process is not implemented and wherein processing block 101 of monitoring for a facial expression in the list continues. 605 illustrates a processing block of implementing the image consulting process, which occurs if there is both a facial expression indication of needing help and an eye tracking indication that a user is studying an imaging feature.

FIG. 7A illustrates a multi-mark up, multi-consultant process. Processing block 700 illustrates providing, for each user, the options to: annotate/perform image processing; classify; and, consult (specific user(s) vs. general open consult). Processing block 701 illustrates performing the smart image consulting process, as described in FIG. 5.

FIG. 7B illustrates an example of the multi-mark up, multi-consultant process. 702 illustrates user A performing annotation(s) of the image and then a general consult. 703 illustrates user B finding the image and studying the annotation(s). Then User B performs some image processing steps including segmentation and filtering. Then User B studies the image. User B does not know how to reliably classify, but does know who is likely to know how to classify the image. Therefore User B performs a consult to a specific user. 704 illustrates user C finding the image, studying user A's annotation and User B's image processing and then performing additional image processing. For example, the user uses the D3D imaging system with viewing of the proper viewing angle. Then, user C performs an additional annotation of an arrow at the site of the lesion. Then, user C performs classification (i.e., gives specific imaging diagnosis). Then user C performs additional annotation (e.g., arrow at site of lesion). Then, user C performs education (e.g., shows similar pathologically proven case) and relays annotation, education, classification and classification to User A. This system is useful because large consulting networks would be possible. For example, if a local hospital performs the imaging consulting process, but no one there confidently knows the diagnosis, then the image can be sent to a larger network, and to specialty centers, such as the Armed Forced Institute of Pathology in Bethesda, Md.

Figure 8A:
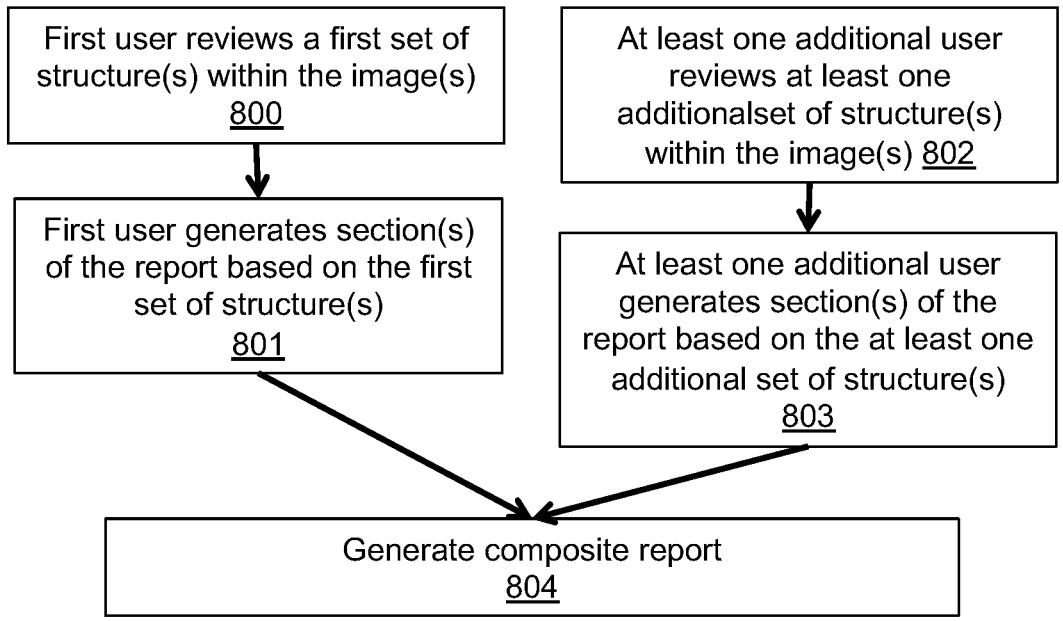
FIG. 8A illustrates a process for multi-user image analysis and reporting.

FIG. 8A illustrates a process for multi-user image analysis and reporting. The multi-user image analysis and reporting has a key role in improving outcomes in emergency situations where a large amount of data needs to be classified in rapid fashion. A good example of this is in trauma where a pan-CT scan (head to toe) is performed. The trauma surgeon needs to know the results almost immediately so they can triage the patient to the operating room for surgery or to the intensive care unit for stabilization. 800 illustrates a first user reviewing a first set of structure(s) within the image(s). 801 illustrates the first user generating section(s) of the report based on the first set of structure(s). 802 illustrates a second user reviewing a second set of structure(s) within the image(s). 803 illustrates the first user generating section(s) of the report based on the first set of structure(s). 804 illustrates generating a composite report.

Figure 8B:
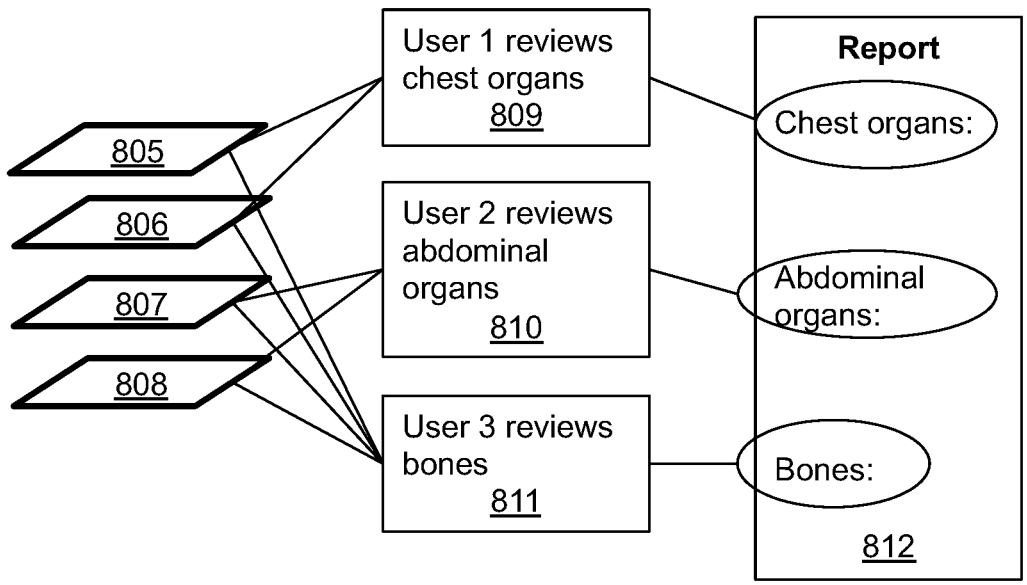
FIG. 8B illustrates an example of multi-user image analysis and reporting of a CT scan of the chest, abdomen and pelvis for performed for trauma.

FIG. 8B illustrates an example of multi-user image analysis and reporting of a CT scan of the chest, abdomen and pelvis for performed for trauma. 805 illustrates a set of CT slices containing chest organs and bones. 806 illustrates a set of CT slices containing chest organs and bones. 807 illustrates a set of CT slices containing abdominal organs and bones. 808 illustrates a set of CT slices containing abdominal organs and bones. 809 illustrates wherein user 1 reviews the chest organs on CT images 805 and 806. 810 illustrates wherein user 2 reviews the abdominal organs on CT images 807 and 808. 811 illustrates wherein user 3 reviews the bones on CT images 809 and 810. 812 illustrates the composite report, which includes a radiology template wherein the chest organs section is completed by user 1, the abdominal organs section is completed by user 2 and the bones section is completed by user 3. The sections can be filled in in real time (and viewed by the trauma surgeon) or upon radiologist approval for fastest delivery of care. In some embodiments, the user can co-sign portions of the report. These portions can be marked up accordingly.

FIG. 9 illustrates examples of image viewing strategies during the multi-mark up, multi-consultant process. To optimize viewing, the user can modify the 3D dataset based on a variety of conventional viewing strategies, such as modifying the visual representation, such as changing the color and transparency, filtering, etc. Additionally, the user can utilize user drawn shapes, arrow(s), 3D cursor(s) and segmentation strategies. In addition, the user can modify the virtual object through a range of advanced viewing strategies. This user can implement a double windowing technique via U.S. Pat. No. 10,586,400, PROCESSING 3D MEDICAL IMAGES TO ENHANCE VISUALIZATION, which is incorporated by reference in its entirety. The user can implement an interaction of 3D dataset with geo-registered tools, as described in U.S. Pat. No. 10,712,837, USING GEO-REGISTERED TOOLS TO MANIPULATE THREE-DIMENSIONAL MEDICAL IMAGES, which is incorporated by reference in its entirety. Examples of geo-registered tools include, but are not limited to the following: knife; scissors; platform; forceps; staples; and, a wide range of other types of surgical tools. The user can perform interaction of 3D dataset with virtual tools, as described in PCT/US19/47891, A VIRTUAL TOOL KIT FOR 3D IMAGING, which is incorporated by reference in its entirety. The user can perform "ghost imaging" per U.S. patent application Ser. No. 16/010,925, INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING, which is incorporated by reference in its entirety. The user can insert flow visualization features, as described in U.S. patent application Ser. No. 16/506,073, A METHOD FOR ILLUSTRATING DIRECTION OF BLOOD FLOW VIA POINTERS, and Ser. No. 16/779,658, 3D IMAGING OF VIRTUAL FLUIDS AND VIRTUAL SOUNDS, which are incorporated by reference in their entirety. The user can perform voxel manipulation strategies, per U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, which is incorporated by reference in its entirety.

FIG. 10 illustrates criteria that an algorithm can use to find the most appropriate consult. First, whether or not a user is actively analyzing a user's current work load (e.g., to prevent from disturbing). Next, analyze past images of each user in the group. High image similarity can be an indication for presenting the image to a user. For example, an artificial intelligence algorithm can analyze a user's prior images that he/she has reported on. If one of them is extremely similar to an image from a first user, then that can be an indication for determining consultant. Next, analyze past reports of each user in the group. High report similarity can be an indication for presenting the image to a user. Next, analyze past consult patterns. Those that were proven to be successful in the past can be used to guide future consultation patterns. For example, feedback from past consult patterns (e.g., satisfaction scores) can be logged and used to determine future consultant patterns. Next, is urgency of the case. If a case is urgent, then this can be a factor in determining consultant patterns. Next, is to determine whether or not user's should be excluded from consulting. For example, a user can turn off a "availability for consulting" button. Next, is to determine which user(s) are available.

FIG. 11A illustrates features of a first user who needs help with a neuroradiology imaging examination. This example assumes a large network of radiologists. 1100 illustrates Radiologist #456 who is a general radiologist with special skill of asbestos related lung disease. Radiologist #456 needs help with a temporal bone imaging examination. As discussed in FIG. 3, factors such as a user's facial expression can be used to determine that a consultation is needed.

FIG. 11B illustrates features of a five users who have expertise in neuroradiology. 1101 illustrates Radiologist #911 who is a neuroradiologist with specialty skills of cerebral vasculitis. 1102 illustrates Radiologist #316 who is a neuroradiologist with specialty skills of PET imaging of dementia. 1103 illustrates Radiologist #200 who is a neuroradiologist with specialty skills of skull base tumors. 1104 illustrates Radiologist #415 who is a neuroradiologist with specialty skills of phacomatoses. 1105 illustrates Radiologist #899 who is a neuroradiologist with specialty skills of temporal bone lesions.

FIG. 11C illustrates the connection of the first user with the optimum consultant. Note that the smart image consulting process, as described in FIG. 5, is performed. As a result, the optimum consultant can receive a consulting RVU.

FIG. 12 illustrates a modified relative value unit (RVU) system based on factors other than just type of imaging examination. Some imaging examinations are normal and a radiologist has little question in the diagnosis. The radiologist quickly reviews and signs a normal report. Some imaging examinations, however, are abnormal and a radiologist has many questions about the image. So much so that a consulting process occurs. When this is the case, the radiologist may unproductive that hour. Furthermore, the radiologist who performs the consultation would also appear unproductive that hour. Therefore, in this situation, an imaging examination is assigned modified RVU. A modified RVU can be modified based on an imaging examination's pathology or lack thereof. For example, if a user reads a normal chest x-ray, the assigned RVU can be a value of 0.1. However, if a user reads an abnormal chest x-ray (contains lung cancer), then the assigned RVU can be at a higher value of 0.2. This system would be useful to better monitor productivity in a fair manner. Other factors can also be used to compute a RVU. For example, an aspect of patient history can be used. For example, indication of the study of a "20 foot fall" can be used to computer a modified RVU. Another such factor is laboratory examination. For example, a user with a WBC count of 20 can be given a higher modified RVU for an imaging examination. Another factor in determining the RVU are factors related to a consulting process (e.g., number of consultations, time involved during consultation). In the broadest sense, an RVU is currently based on only the type of imaging examination. In this patent, a modified RVU score can be utilized based on at least one additional factor. This modified RVU system is important because it can more fairly assess productivity amongst radiologists. The number of examinations, number of consultations, and number of referrals to consultant (i.e., by 3rd user) can be used to determine productivity.

FIG. 13 illustrates a worklist for radiologists. The first column illustrates a list of unread examinations. For example, these can be a set of images that are recently acquired by the technologists and have never been opened by any radiologist. A radiologist who interprets and examination and files a report would receive an RVU or modified RVU per FIG. 12. The second column illustrates a list of general (open to anyone) cases needing consultation. For example, Dr. J, a radiologist, may be confused on how to measure a scoliosis film and therefore performs annotations on the image and sends it to the general consultation list. Dr. K, a radiologist, sees the image pop up, knows how to perform the measurement, performs the consultation to Dr. J. For the consulting process to work optimally (and fairly), Dr. K would receive some RVU or the like. The third column illustrates a list of general (only seen by you) cases needing consultation. Assume that this list is seen by Dr. W. A case sent only to Dr. W would be shown in this third column. A case sent from Dr. J to Dr. K would not be seen in Dr. W's third column. In some cases, Dr. W may see the case, not know what it is, and then kick it back to the second column (general pool) where any radiologist can review the case. Dr. W could, as previously discussed, also pass the annotated image (e.g., visible boundary) into the general pool. Additionally, the number of times a case is passed can be used in the analysis (e.g., of a modified RVU).

What is claimed is:

1. A method comprising:
   displaying an image to a first user from a group of users;
   selecting a second user from said group of users for classification of said image
      wherein said second user is a most appropriate consult from said group of users,
      wherein said second user is qualified with respect to a type of said image,
      wherein said second user is qualified with respect to an imaging feature of said image,
      wherein said second user is qualified to classify the image,
      wherein said selection of said second user is performed by a computer system,
      wherein said computer system performs an algorithm to select said second user,
      wherein said algorithm comprises at least one of the group consisting of:
         a computer algorithm; and
         an artificial intelligence algorithm;
      wherein said algorithm incorporates feedback within said group of users,
      wherein said feedback incorporates a rating system of prior consults within said group of users,
   upon an input from the first user, presenting the image to the second user;
   receiving a classification of said image by said second user; and
   presenting said classification of said second image to said first user.

2. The method of claim 1 further comprising sending said image into a bin where said group of users can view said image.

3. The method of claim 2 further comprising wherein a third user reviews said selection of said second user.

4. The method of claim 1 further comprising wherein a set of characteristics is used to select the second user.

5. The method of claim 4 further comprising wherein a characteristic in the set of characteristics comprises prior image classifications.

6. The method of claim 4 further comprising wherein a characteristic in the set of characteristics comprises prior images.

7. The method of claim 4 further comprising wherein a characteristic in the set of characteristics includes feedback from past consult patterns wherein feedback comprises rating(s) of classification(s) of said second user.

8. The method of claim 4 further comprising wherein a characteristic in the set of characteristics includes an availability user(s) in the group.

9. The method of claim 4 further comprising wherein a characteristic in the set of characteristics includes an urgency of the image.

10. The method of claim 1 further comprising wherein, before presenting the image to the second user, the first user performs at least one of the group comprising: image processing; annotations on the image; and, selecting a portion of the image for analysis.

11. The method of claim 1 further comprising wherein, before presenting the classification to the first user, the second user performs at least one of the group comprising: image processing; annotations on the image; selecting a portion of the image for analysis; and, presentation of the image to at least one additional user.

12. The method of claim 1 further comprising wherein the second user performs a teaching session to the first user wherein the teaching session comprises at least one of the group of: image processing; and, image annotation.

13. The method of claim 1 further comprising wherein the selecting a second user occurs based on an input from the first user wherein the input consists of at least one of the group of:
   activating, by the first user, a help button;
   activating, by the first user, a consult request;
   detecting, by a camera, that the first user has a predetermined facial expression;
   detecting, by a camera, that the first user has a predetermined eye pattern;
   detecting, by a camera, that the first user has a predetermined combination of facial expression and eye pattern; and
   detecting, by a second computer algorithm, that there is a difference between a classification of said first user and a classification by a second artificial intelligence algorithm.

14. The method of claim 1 further comprising a reward system to at least one of the group comprising: the first user; the second user; and, an additional user.

15. The method of claim 1 further comprising generating a modified relative value unit (RVU) of an imaging examination based on the presence of at least one imaging finding in the imaging examination.

16. The method of claim 1 further comprising generating a modified relative value unit (RVU) of an imaging examination based on at least one of the group consisting of: indication of said imaging examination; laboratory data; consultations; and, urgency of said imaging examination.

17. The method of claim 1 further comprising wherein a classification accuracy of users in said group of users is determined.

18. The method of claim 1 further comprising wherein a report of said first user indicates an image consult.

19. A non-transitory storage medium storing a program that causes a computer to execute the program, the program configured to:
   display an image to a first user from a group of users;
   select a second user from said group of users for classification of said image
      wherein said selecting said second user is said most appropriate consult from said group of users,
      wherein said second user is qualified with respect to a type of said image,
      wherein said second user is qualified with respect to an imaging feature of said image,
      wherein said second user is qualified to classify the image,
      wherein said computer software executes an artificial intelligence algorithm to perform said selection of said second user,
      wherein said artificial intelligence algorithm learns from feedback of prior consults within said group of users,
      wherein said feedback incorporates a rating system,
   display said image to said second user upon an input from said first user;
   receive a classification of said image by said second user; and
   present said classification of said image to said first user.

20. A computer system comprising:
   a memory;
   a processor;
   a communications interface;

an interconnection mechanism coupling the memory, the processor and the communications interface; and wherein the memory is encoded with an application for determining a most appropriate consult for an image, that when performed on the processor, provides a process for processing information, the process causing the computer system to perform the operations of:

displaying said image to a first user from a group of users;

selecting a second user from said group of users for classification of said image
- wherein said second user is said most appropriate consult from said group of users,
- wherein said second user is qualified with respect to a type of said image,
- wherein said second user is qualified with respect to an imaging feature of said image,
- wherein said second user is qualified to classify the image,
- wherein said computer system executes an artificial intelligence algorithm to perform said selection of said second user,
- wherein said artificial intelligence algorithm learns from feedback of prior consults within said group of users,
- wherein said feedback incorporates a rating system, upon an input from said first user, displaying said image to said second user;

receiving a classification of said image by said second user; and presenting said classification of said image to said first user.

\* \* \* \* \*